(12) United States Patent
Klein

(10) Patent No.: US 7,364,545 B2
(45) Date of Patent: Apr. 29, 2008

(54) METHOD OF MEASURING BLEEDING VOLUME

(76) Inventor: Jeffrey A. Klein, 30280 Rancho Viejo Rd., San Juan Capistrano, CA (US) 92675

( * ) Notice: Subject to any disclaimer, the term of this patent is extended or adjusted under 35 U.S.C. 154(b) by 527 days.

(21) Appl. No.: 11/110,395

(22) Filed: Apr. 20, 2005

(65) Prior Publication Data

US 2006/0241504 A1    Oct. 26, 2006

(51) Int. Cl.
*A61B 5/00*    (2006.01)

(52) U.S. Cl. ............... 600/369; 600/300; 600/368; 128/DIG. 22

(58) Field of Classification Search ............ 600/369, 600/371; 128/DIG. 22; 73/64.41
See application file for complete search history.

(56) References Cited

U.S. PATENT DOCUMENTS

| | | | |
|---|---|---|---|
| 3,712,293 A | 1/1973 | Mielke | |
| 4,078,552 A | 3/1978 | Chen et al. | |
| 4,438,770 A | 3/1984 | Unger et al. | |
| 4,799,488 A * | 1/1989 | Mintz | 600/369 |
| 5,613,491 A * | 3/1997 | Kanner et al. | 600/369 |

\* cited by examiner

*Primary Examiner*—Robert L. Nasser, Jr.
*Assistant Examiner*—Patricia C Mallari
(74) *Attorney, Agent, or Firm*—Stetina Brunda Garred & Brucker

(57) ABSTRACT

A method of measuring blood clotting ability of a patient. A known volume of blood is dispensed on a reference disc of blotter paper, such that at least one reference blotch is formed on the reference disc. The surface area of the reference blotch formed on the reference disc, such that a relationship between the volume of blood and the surface area of the reference blotch can be obtained. An incision is made at the patient. A piece of blotter paper to the incision is applied to the incision to collect blood flowing therefrom, such that at least one blotch is formed on the piece of blotter paper. The surface area of the blotch formed on the piece of blotter paper is measured. The volume of the blood absorbed blood by the blotter paper is calculated according to the relationship between the blood volume and the surface area of the blotch.

14 Claims, 3 Drawing Sheets

METHOD OF MEASURING BLEEDING VOLUME

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

The present invention relates in general to a method of measuring blood clotting ability, that is, the tendency of a patient to bleed, and more particularly, to a method which provides accurate quantitative information of blood clotting ability and bleeding tendency of the patient by precisely measuring the bleeding volume of the patient.

Blood clotting is a process by which the blood coagulates to form solid masses or clots following a wound or trauma. The ability of blood clotting is typically measured by a technique known as IVY Bleeding Time named after Mr. Ivy. The IVY bleeding Time is a widely used test for bleeding tendency that measures the length of time that bleeding continues after an incision is made in the forearm of a patient. To measure the bleeding time of the patient, a round disc of blotter paper is used. The edge of the disc of blotter paper is applied tangentially to the incision to absorb the blood by capillary action. After an interval of 30 seconds, the disc is rotated to a new contact point so that the small blotches of blood are distributed around the periphery of the blotter paper. Typically, the successive blotches of blood become smaller and smaller. By counting the number of blotches, and dividing the total number of the blotches by 2, one can derive the duration of bleeding in minutes. The duration of bleeding time is normally less than 7 minutes.

With respect to surgical complications and patient safety, the duration of bleeding is not as important as the volume of bleeding. If one could measure the volume of blood lost during an IVY Bleeding Time, then a much more powerful and clinically relevant predictor of excessive surgical bleeding would be provided. For example, just prior to surgery, a medical practitioner would be able to assess the probability that the patient had recently taken an aspirin; and therefore, the risk of surgical bleeding complications could be increased.

Therefore, a substantial need exists in the art to develop a method for measuring not only the bleeding time, but also the blood volume of a patient to ensure patient safety and prevent possible surgical complication.

BRIEF SUMMARY OF THE INVENTION

The present invention provides a method of measuring blood clotting ability of a patient comprising the following step. A known volume of blood is dispensed on a reference disc of blotter paper, such that at least one reference blotch is formed on the reference disc. The surface area of the reference blotch formed on the reference disc is measured, such that a relationship between the volume of blood and the surface area of the reference blotch can be obtained. An incision is made on the patient, and a piece of blotter paper is applied to the incision to collect blood from the incision, such that at least one blotch is formed on the piece of blotter paper. The surface area of the blotch formed on the piece of blotter paper is measured. The volume of the blood absorbed by the blotter paper is calculated according to the relationship between the blood volume and the surface area of the blotch.

In one embodiment, a micropipette is used to dispense the known volume of blood on the reference disc. The steps of applying the piece of blotter paper to the incision and the step of calculating the blood volume are repeated until the incision stops bleeding, and the total volume of the blood collected from the incision can be obtained by adding the blood volumes of all the blotches. According to specific need, the bleeding time of the patient may also be counted at the time when the volume of blood is measured.

To measure the surface area of the reference blotch, the image of the reference blotch is reprinted on a piece of paper. A plurality of paper squares each having a unit surface area is provided. The blotch image is fitted with a first number of the paper squares, and the first number of paper squares covers an interior surface area of the blotch. The blotch image is further fitted with a second number of paper squares, wherein the second number of paper squares covers the both interior surface area and a periphery of the blotch only. An average of the first and second numbers is obtained. The average is multiplied with the unit surface area to obtain the surface area of the blotch image. Preferably, the reference blotch is magnified by a magnification factor before being reprinted. Therefore, the surface area of the blotch image has to be divided by the magnification factor to derive the real surface of the blotch. The incision is preferably made in the skin of a forearm of the patient, and the length and depth of the incision are preferably about 4 mm and about 1 mm, respectively. The piece of blotter paper is preferably tangentially to the incision.

To obtain a more precise measurement of the blood volume and the blood clotting ability of the patient, the step of measuring the surface area of the reference blotch may further comprise the following steps. A reference area with a unit surface area is scanned to obtain a reference image. The reference image representing the unit surface area is stored into a memory. The reference blotch is optically scanned and compared with the reference image, such that the surface area of the reference blotch can be derived. Similarly, the step of measuring the surface area of the blotch formed on the piece of blotter paper also includes scanning the blotch formed on the piece of blotter paper and comparing the scanned blotch with the reference image to derive the surface area of the blotch.

The present invention further provides an alternate method of measuring blood clotting ability of a patient, which comprises the following steps. A known volume of blood is dispensed around a periphery of a reference disc of blotter paper, such that various shapes of reference blotches with the same surface area are formed. This step is repeated by dispensing different volumes of blood on a set of reference discs of blotter paper. An incision is made on a patient, and a piece of blotter paper is applied to the incision, such that a plurality of blotches is formed on the piece of blotter paper. The blotches formed on the piece of blotter paper are compared with the reference blotches, such that the surface areas and blood volumes of the blotches on the piece of blotter paper can be estimated from the reference blotches matching therewith. The blood volumes represented by all the blotches formed on the piece of blotter paper are then added together to show the total blood volume of the incision. The steps applying the piece of blotter paper to adding the blotches are repeated until the patient stop bleeding from the incision.

BRIEF DESCRIPTION OF THE DRAWINGS

These, as well as other features of the present invention, will become apparent upon reference to the drawings wherein.

DETAILED DESCRIPTION OF THE INVENTION

Figure 1:
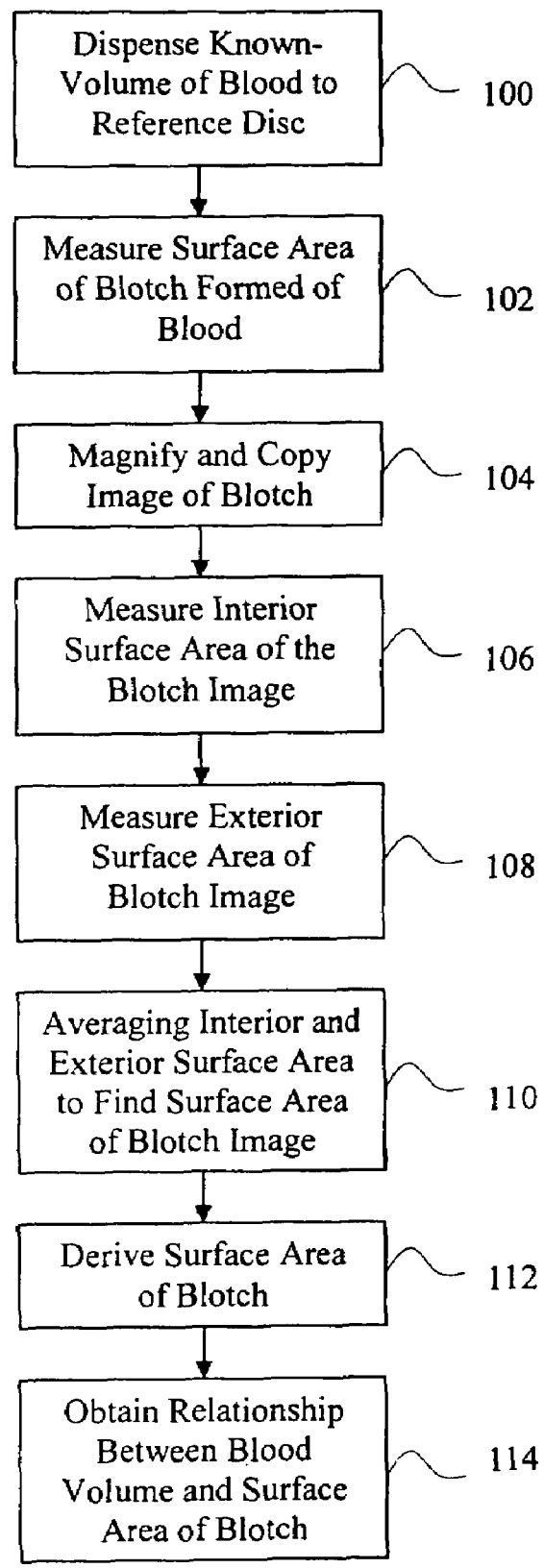
FIG. 1 comprises a flow chart of a method to obtain relationship between blood volume and surface area of a blotch formed of absorbed blood.

Referring now to the drawings wherein the showings are for purpose of illustrating preferred embodiments of the present invention only, and not for purposes of limiting the same. As shown in FIG. 1, the present invention provides a method for measuring not only the bleed time, but also the blood volume for a patient, particularly at the time prior to a surgery.

To measure the blood volume of a patient, the relationship between the blood volume and the surface area of blotches formed of blood on the blotting paper is determined by the method as shown in FIG. 1. As shown, in step 100, a micropipette is used to dispense a known volume of blood onto a piece of standard blotter paper. After the blood is applied to the blotter paper, the surface area of blotches formed of the absorbed blood is measured in step 102. Preferably, the blotter paper which absorbs the blood is magnified by a magnification factor, and the magnified images are copied or reprinted onto a piece of high-resolution paper in step 104. In steps 106 and 108, a plurality of paper squares with a known surface area is provided to measure an interior surface area and an exterior surface area of the blotch. In this embodiment, the Euclid method is used to measure the surface area of the blotches. That is, in step 106, a first number of the paper squares is used to fit within the blotches. In this step, the first number of the paper squares fitting within the blotches does not exceed or cover the boundary or periphery of the blotches, that is, the surface area covered by the first number of paper squares is the interior surface area of the blotch, which is slightly smaller than the real surface area of the blotch. By multiplying the first number with the surface of each paper square, the interior surface of the blotch can be obtained. In step 108, a second number of the paper squares is used to fit over the blotches. The second number of paper squares does not only cover the interior surface of the blotches, but also covers the boundary, that is, the periphery of the blotches. Therefore, the area covered by the second number of paper squares represents the exterior surface area of the blotch, which is slightly larger than the real surface area of the blotch. The second number is then multiplied with the surface area of each paper square to obtain the exterior surface area of the blotch. In step 110, the real surface of the blotch can be obtained by calculating an average of the interior surface area and exterior surface is obtained. In step 112, the surface area of the blotches is obtained by the dividing surface area of the images of the blotches by the magnification factor. In step 114, the relationship between the blood volume and the surface area of the blotches formed of the blood can be obtained. For example, one can derive the blood volume represented by each unit surface area of the blotches formed of the blood. Empirical data has found that the volume of blood deposited on the blotting paper has a substantially linear behavior with respect to the surface area of blotches formed of the blood. Although this method provides a relatively precise measurement of the surface areas of blotches, it is not a very time-efficient method. In a routine clinical setting such as a doctor's office, surgery center or hospital, it would be excessively time consuming to measure surface areas using a photocopier and counting small squares on graph paper. Therefore, alternate methods are further provided in the present invention.

Figure 2:
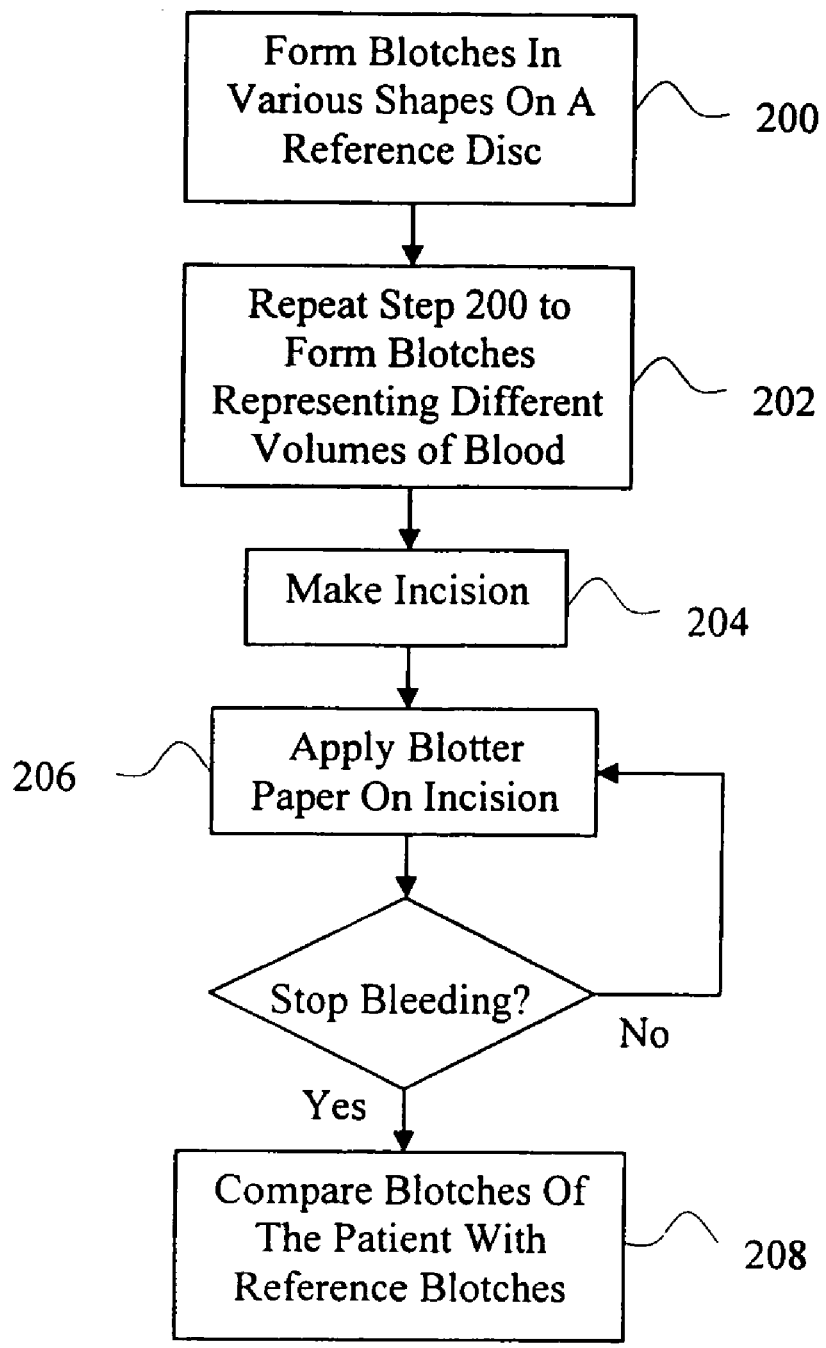
FIG. 2 comprises a flow chart of a visual comparison method for measuring blood clotting ability of a patient.

FIG. 2 illustrates the flow chart of an alternate method for measuring the blood clotting ability of a patient. As mentioned above, empirical data has found that the volume of blood absorbed by a blotting paper from an incision of the patient is substantially linear to the total surface area of the blotches of absorbed blood along the blotter paper edge. Therefore, by measuring the surface area of the blotches, the volume of the blood obtained from the incision can be calculated. Further, as the blotches collected from the patient are typically in different shapes, blotches in various shapes are made with known volume of blood as a reference to compare with the blotches formed of absorbed blood obtained from the incision made in the patient.

As shown in FIG. 2, a micropipette is used to dispense a predetermined volume of blood at various positions of a periphery of a reference disc. As a result, multiple blotches in different shapes are formed on the reference disc. As the blotches are formed of the same amount of blood, the blotches in various shapes have the same surface area. In step 202, a set of reference discs on which blotches are formed to represent different blood volumes such as 1, 2, 5, 10, 20, 30, 40 and 50 micro-liters is reproduced by performing the step 200 on a plurality of reference discs. In this manner, different surface areas of blotches in various shapes are sampled printed for reference. In step 204, an incision is made in the skin of the forearm of the patient. Preferably, similarly to the IVY Bleeding Time Test, the incision is 4 mm long and 1 mm deep. Simultaneously, a blood pressure tourniquet located on the arm is pumped to approximately 70 mm of mercury pressure in order to assure a standardized capillary blood pressure. In step 206, a piece of blotter paper is applied to the incision tangentially to absorb the blood oozing therefrom. As a result, a plurality of blotches is formed along the periphery of the piece of blotter paper. Step 206 is repeated until the patient stops bleeding. In step 208, the blotches collected in the blotter paper are then visually compared to the reference blotches formed on the reference discs. As various shapes of blotches with various surface areas that represent various volumes of blood have been obtained, the blood volume of each blotch formed on the blotter paper can be precisely estimated in step 208. This method is simple and sufficiently accurate to detect a grossly abnormal bleeding volume. However, such visual comparison method is not sufficiently sensitive to detect subtle differences that might be clinically important.

Figure 3:
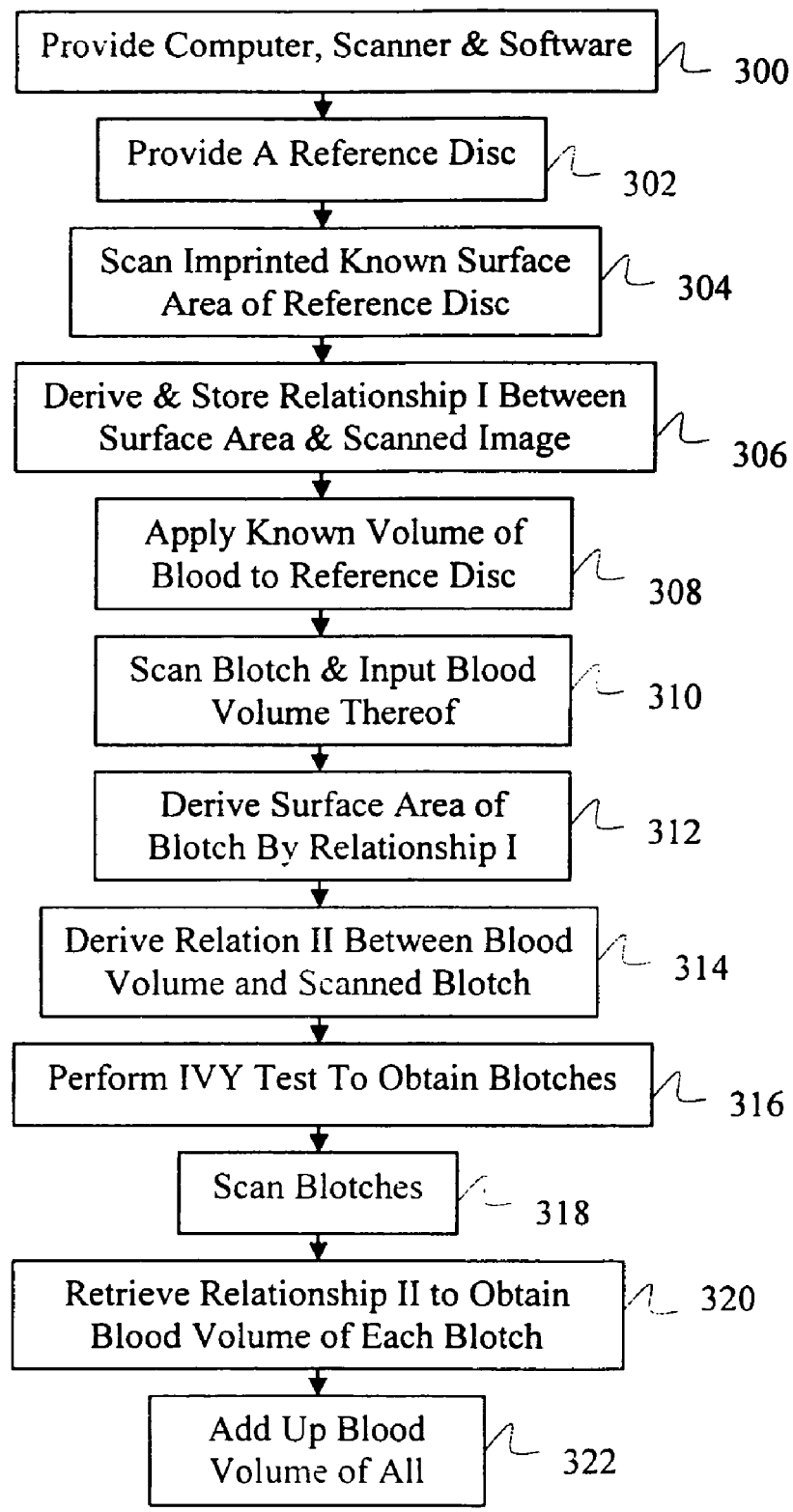
FIG. 3 comprises a flow chart of a computerized method for measuring blood clotting ability of a patient.

FIG. 3 shows a computerized method for measuring blood clotting ability for a patient. In step 300, a computer, a scanner, and a software are provided. The computer includes a desktop, laptop, palm-pilot computer, for example; and the software includes commercially available program operative to precisely analyze and measure surface area of a scanned image such as Adobe Photoshop or other photo-processing programs or applications. The computer comprises at least a central processing unit and a memory for executing the software and storing required information, respectively. In step 302, a reference disc of blotter paper is provided. The reference disc is placed in a clear or transparent plastic envelope to protect from personnel or equipment contamination with blood born pathogens. A part of the reference disc, preferably the center of the reference disc with a size of 1 cm$^2$ is imprinted and scanned by the scanner in step 304. Thereby, a relationship between the scanned image and the surface area of the scanned image is obtained and stored in the memory in step 306. In step 308, a known volume of blood is applied to another reference disc of blotter paper, or the reference disc removed from the plastic envelope, such that a blotch is formed. The blotch formed on the reference disc is then scanned by the scanner to obtain the image thereof, and the blood volume represented by the scanned image is input to the computer in step 310. The relationship between the surface area and the scanned image stored in the memory is retrieved to calculate the real surface area of the blotch in step 312. Thereby, a relationship between the volume of blood and the scanned image is obtained in stored in the memory in step 314. In step 316, the IVY Bleeding Time Test is performed. That is, an incision is made at the forearm of the patient, and the blood of the incision is collected by applying blotter paper to the incision until the patient stop bleeding. The blood collected by the blotter paper is then dried to form various shapes and surface areas of blotches. To avoid personnel and equipment contamination, similarly, the blotter paper is placed in clear plastic bags. The blotches are then scanned by the scanner, and the scanned images of the blotches are input to the computer in step 318. In step 320, the relationship between the blood volume and the scanned image is retrieved from the memory, and the blood volume represented by each blotch is obtained. In step 322, the total blood volume is obtained by adding the blood volume represented by each of the blotches obtained from the incision.

This disclosure provides exemplary embodiments of a method of measuring blood clotting ability of a patient. The scope of this disclosure is not limited by these exemplary embodiments. Numerous variations, whether explicitly provided for by the specification or implied by the specification, such as variations in shape, structure, dimension, type of material or manufacturing process may be implemented by one of skill in the art in view of this disclosure.

What is claimed is:

1. A method of measuring blood clotting ability of a patient, comprising:
    a) dispensing a known volume of blood on a reference disc of blotter paper, such that at least one reference blotch is formed on the reference disc;
    b) measuring a surface area of the reference blotch formed on the reference disc;
    c) obtaining a relationship between the volume of blood and the surface area of the reference blotch;
    d) making an incision on the patient;
    e) applying a piece of blotter paper to the incision, such that at least one blotch is formed on the piece of blotter paper;
    f) measuring a surface area of the blotch formed on the piece of blotter paper; and
    g) calculating the volume of the blood formed on the piece of blotter paper in accordance with the relationship between the blood volume and the surface area of the reference blotch, a sum of the calculated blood volume being indicative of the blood clotting ability of the patient.

2. The method of claim 1, wherein step (a) further comprises using a micropipette to dispense a known volume of blood on the reference disc.

3. The method of claim 1, further comprising repeating steps (e) to (g) until the patient stops bleeding.

4. The method of claim 3, further comprising adding up the blood volume of all blotches on all pieces of blotter paper collected from the incision.

5. The method of claim 3, further comprising counting the bleeding time of the patient.

6. The method of claim 1, wherein step (b) further comprises:
    reprinting the reference blotch on a piece of paper to obtain a blotch image;
    providing a plurality of paper squares each having a unit surface area;
    fitting the blotch image with a first number of paper squares, wherein the first number of paper squares covers an interior surface area of the blotch;
    fitting the blotch image with a second number of paper squares, wherein the second number of paper squares covers the interior surface area and a periphery of the blotch only; and
    obtaining an average of the first and second numbers; and
    multiplying the average with the unit surface area to obtain the surface area of the blotch.

7. The method of claim 6, further comprising:
    magnifying the reference blotch by a magnification factor before reprinting; and
    dividing the surface area obtained from the step multiplying the average with the unit surface area by the magnification factor.

8. The method of claim 1, wherein step (d) comprising making the incision in the skin of a forearm of the patient.

9. The method of claim 1, wherein step (d) comprises making the incision with a length of about 4 mm and a depth of about 1 mm.

10. The method of claim 1, wherein step (e) comprises applying the piece of blotter paper tangentially to the incision.

11. The method of claim 1, wherein step (b) comprises:
    scanning a reference area with a unit surface area to obtain a reference image;
    storing the reference image into a memory;
    scanning the reference blotch;
    comparing the scanned reference blotch with the reference image to derive the surface area of the reference blotch.

12. The method of claim 11, wherein step (f) comprises:
    scanning the blotch formed on the piece of blotter paper; and
    comparing the scanned blotch with the reference image to derive the surface area of the blotch.

13. A method of measuring blood clotting ability of a patient, comprising:
    a) dispensing a known volume of blood around a periphery of a reference disc of blotter paper, such that a plurality of reference blotches in various shapes with the same surface area is formed;
    b) repeating step (a) by dispensing different volumes of blood on a set of reference discs of blotter paper;
    c) making an incision on a patient;
    d) applying a piece of blotter paper to the incision, such that a plurality of blotches is formed on the piece of blotter paper;

e) comparing the blotches formed on the piece of blotter paper with the reference blotches, such that the surface areas and blood volumes of the blotches on the piece of blotter paper can be derived from the reference blotches matching therewith; and f) adding up the blood volumes represented by all the blotches formed on the piece of blotter paper, a sum of the added up blood volumes being indicative of the blood clotting ability of the patient.

14. The method of claim 13, further comprising repeating step (d) to (f) until the patient stops bleeding from the incision.

* * * * *